United States Patent [19]

Prücher

[11] Patent Number: 4,954,499
[45] Date of Patent: Sep. 4, 1990

[54] PYRIDAZINONE DERIVATIVES

[75] Inventor: Helmut Prücher, Heppenheim, Fed. Rep. of Germany

[73] Assignee: Merck Patent Gesellschaft Mit Beschrankter Haftung, Darmstadt, Fed. Rep. of Germany

[21] Appl. No.: 156,512

[22] Filed: Feb. 16, 1988

[30] Foreign Application Priority Data

Feb. 17, 1987 [DE] Fed. Rep. of Germany ....... 3704879

[51] Int. Cl.$^5$ .................. C07D 413/04; A61F 31/535
[52] U.S. Cl. ..................................... 514/247; 544/239; 544/241
[58] Field of Search ....................... 544/238, 239, 241; 514/247

[56] References Cited

U.S. PATENT DOCUMENTS 4,816,454 3/1989 Zoller et al. ..................... 544/238

FOREIGN PATENT DOCUMENTS 2922336 11/1980 Fed. Rep. of Germany .

OTHER PUBLICATIONS

CA 109 (23) 211070e (1988).
CA 98 198261(a) p. 659 (1983).
CA 94 175143 (s) (1981).
Chemical Abstracts 112 21004 (a) (1990).
Chemical Abstracts 112 55899 (m) (1990).

Primary Examiner—Nicholas S. Rizzo
Attorney, Agent, or Firm—Millen, White & Zelano

[57] ABSTRACT

A pyridizinone derivative of the formula I

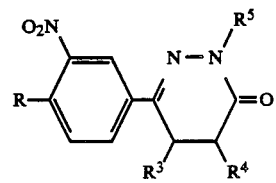

wherein
R is F, Cl, Br, I or $R^1R^2N$,
$R^1$ and $R^2$ are each H, $C_{1-4}$-alkyl or benzyl,
$R^3$, $R^4$ and $R^5$ are each H or $C_{1-4}$-alkyl and
wherein it is only possible for R to be benzylamino, $R^3$ to be $CH_3$ and $R^4$ to H at the same time if $R^5$ is alkyl, and salts thereof display positive inotropic properties and vasodilative properties and can be used, in particular, as intermediate products in the production of other pharmaceutical agents.

20 Claims, No Drawings

PYRIDAZINONE DERIVATIVES

BACKGROUND OF THE INVENTION

The invention relates to new pyridazinone derivatives of the formula I

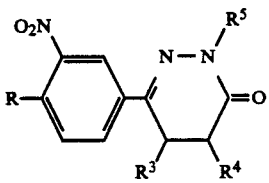

wherein
R is F, Cl, Br, I or $R^1R^2N$,
$R^1$ and $R^2$ are each H, alkyl or benzyl,
$R^3$, $R^4$ and $R^5$ are each H or alkyl and
the alkyl groups each contain 1–4 C atoms, but wherein it is only possible for R to be benzylamino, $R^3$ to be $CH_3$ and $R^4$ to be H at the same time if $R^5$ is alkyl, and also to salts thereof.

A similar compound "5-methyl-6-(3-nitro-4-benzylaminophenyl)-4,5-dihydro-2H-pyridazin-3-one" (corresponding to I with R being benzylamino, $R^3$ being $CH_3$ and $R^4$ and $R^5$ being H) is mentioned in German Offenlegungsschrift No. 2,922,336, but a process for its preparation is not mentioned therein.

SUMMARY OF THE INVENTION

It is an object of this invention to find new compounds having valuable properties, in particular, compounds which can be used for the preparation of medicaments.

Upon further study of the specification and appended claims, further objects and advantages of this invention will become apparent to those skilled in the art.

These objects have been satisfied by the provision of compounds of the formula

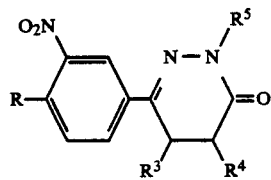

wherein
R is F, Cl, Br, I or $R^1R^2N$,
$R^1$ and $R^2$ are each independently H, $C_{1-4}$-alkyl or benzyl,
$R^3$, $R^4$ and $R^5$ are each independently H or $C_{1-4}$-alkyl, or a pharmaceutically acceptable salt thereof, wherein, if R is benzylamino, $R^3$ is $CH_3$ and $R^4$ is H, $R^5$ is $C_{1-4}$-alkyl.

DETAILED DESCRIPTION

It has been found that these compounds and their salts possess valuable pharmacological properties and are well tolerated. In particular, they display an action on the force of myocardial contraction (positive inotropic effectiveness); the substances also have a vasodilative action and hence promote blood flow. The vasodilative action and the action on the heart can be determined, for example, on narcotized or conscious dogs, cats, monkeys or mini-pigs; and the positive inotropic action can also be determined on isolated heart preparations (for example the atrium, papillary muscle or perfused whole heart) of rats, Guinea pigs, cats or dogs, for example by methods such as are described in Arzneimittelforschung, volume 31 (I), No. 1a (1981), pages 141 to 170, or by Schliep et al. in the 9th International Congress of Pharmacology, London, Abstracts of papers 9P.

Antithrombotic properties and properties which inhibit the aggregation of platelets and influence the form of erythrocytes are also found. The influence on the platelet function in the sense of inhibiting aggregation can be demonstrated on rats ex vivo in Born's test (Nature 194, 927–929, 1962). The antithrombotic action manifests itself in the prolongation of bleeding time by Stella's method (Thrombos. Res. 7, 709–716, 1975), in reduction of the thrombus weight in the cold-induced thrombosis of the jugular vein in rats by Meng's method (Ther. Ber. 47, 69–79, 1975) and in the increase in the laser pulses required for complete thrombosis at the mesenteric venule of rats, in accordance with the modification of Kovacs' method (Microvasc. Res. 6, 194–201, 1973).

The advantageous action on the deformability of erythrocytes can be demonstrated in the Nucleopore filter by Schmid-Schönbein's method (Pflüger's Archiv 338, 93–114, 1973). Advantageous effects on the fibrinolysis/euglobulinlysis time by V. Kaulla's method (Progr. Chem. Fibrinol. Thrombol. 1, 131–149, 1975; ed. J. F. Davidson, Raven Press, N.Y.) can also be observed.

The compounds can therefore be used as active compounds for medicaments in human and veterinary medicine. In particular, however, they can be used as intermediate products for the preparation of further active compounds for medicaments, for example those described in German Offenlegungsschrift No. 3,505,609. Thus it is possible, for example by hydrogenating compounds of the formula I wherein R is an $R^1R^2N$ group, to obtain the corresponding 3-amino derivatives, for example 6-(3,4-diaminophenyl)-5-methyl-2,3,4,5-tetrahydropyridazin-3-one [compare German Offenlegungsschrift No. 3,505,609, Example 1; described there as "5-methyl-6-(3,4-diaminophenyl)-4,5-dihydropyridazin-3-one"].

Alkyl in the formulae is preferably unbranched, preferably has 1–3 C atoms and is preferably methyl and also preferably ethyl or propyl, and also isopropyl, butyl, isobutyl, sec.-butyl or tert.-butyl.

The group $R^1R^2N$ is preferably amino, methylamino, ethylamino, benzylamino, N-benzyl-N-methylamino or N-benzyl-N-ethylamino, and also preferably propylamino, dimethylamino, methylethylamino, diethylamino or dipropylamino, and also, for example, isopropylamino, butylamino, isobutylamino, sec.-butylamino, tert.-butylamino, diisopropylamino, dibutylamino, diisobutylamino, di-sec.-butylamino, di-tert.-butylamino, dibenzylamino, N-benzyl-N-propylamino, N-benzyl-N-butylamino, N-benzyl-N-isobutylamino, N-benzyl-N-sec.-butylamino or N-benzyl-N-tert.-butylamino.

Radicals R which are particularly preferred are Cl and $H_2N$, and also F, methylamino, ethylamino, benzylamino, N-benzyl-N-methylamino or N-benzyl-N-ethylamino.

The radicals $R^1$ and $R^2$ are preferably H, methyl, ethyl or benzyl. $R^3$ is preferably alkyl and particularly methyl. $R^4$ and $R^5$ are each preferably H or $CH_3$, especially H.

The invention relates, in particular, to compounds of the formula I in which at least one of the radicals mentioned has one of the preferred meanings indicated above. Some preferred groups of compounds can be expressed by means of the following partial formulae Ia to Ig, which correspond to the formula I and in which the radicals not designated in detail have the meaning indicated in the formula I, but in which:

in Ia $R^3$ is alkyl having 1–4 C atoms;
in Ib $R^3$ is $CH_3$;
in Ic
   R is F, Cl, $H_2N$, methylamino, ethylamino, benzylamino, N-benzyl-N-methylamino or N-benzyl-N-ethylamino,
   $R^3$ and $R^5$ are each H or $CH_3$ and
   $R^4$ is H;
in Id
   R is F, Cl, $H_2N$, methylamino, ethylamino, benzylamino, N-benzyl-N-methylamino or N-benzyl-N-ethylamino,
   $R^3$ is $CH_3$,
   $R^4$ is H and
   $R^5$ is H or $CH_3$;
in Id R is F, Cl, Br or I;
in Ie R is $R^1R^2N$;
in If
   R is F, Cl, $H_2N$, N-benzyl-N-methylamino or N-benzyl-N-ethylamino,
   $R^3$ is $CH_3$,
   $R^4$ is H and
   $R^5$ is H or $CH_3$; and
in Ig
   R is F or Cl,
   $R^3$ is $CH_3$ and
   $R^4$ and $R^5$ are each H.

The compounds of the formula I are, moreover, prepared by methods which are known per se, such as are described in the literature (for example in the standard works such as Houben-Weyl, Methoden der Organischen Chemie ("Methods of organic chemistry"), Georg-Thieme-Verlag, Stuttgart), in particular under reaction conditions which are known and suitable for the reactions mentioned. In this respect it is also possible to make use of variants which are known per se but are not mentioned here in detail.

If desired, the starting materials can also be formed in situ, in a manner in which they are not isolated from the reaction mixture, but are immediately reacted further to give the compounds of the formula I. On the other hand, it is possible to carry out the reaction in stages, and to isolate further intermediate products.

The invention also relates to a process for the preparation of pyridazinone derivatives of the formula I and salts thereof which is characterized in that a keto acid of the formula II

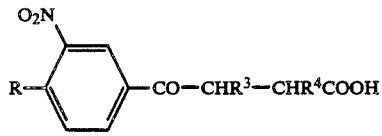

wherein R, $R^3$ and $R^4$ have the meanings indicated, or one of its reactive derivatives is reacted with a hydrazine of the formula $R^5$—NH—$NH_2$ (wherein $R^5$ has the meaning indicated or with one of its reactive derivatives, and/or a functional group in a compound of the formula I is converted into another functional group, and, if desired, a base of the formula I is converted into one of its salts by treatment with an acid.

The carboxylic acids of the formula II can be prepared by methods which are known per se, for example analogously to German Offenlegungsschrift No. 2,837,161.

Suitable reactive derivatives of the carboxylic acids of the formula II are, in particular, the esters, for example the alkyl esters wherein the alkyl group preferably has 1–4 C atoms, especially the methyl and ethyl esters, and also the nitriles and, for example, the acid chlorides or acid bromides and the amides. Further suitable reactive derivatives of the carboxylic acids of the formula II can be formed in situ during the reaction, without being isolated. These include, for example, the hydrazones of the formula Ar—C(=NNHR$^5$)—CHR$^3$—CHR$^4$—COOH and the hydrazides of the formula Ar—CO—CHR$^3$—CHR$^4$—CO—NHNHR$^5$ (wherein Ar is the 3-nitro-4-R-phenyl radical).

Examples of suitable reactive derivatives of the hydrazine of the formula $R^5$—NH—$NH_2$ are the corresponding hydrazine hydrates, acethydrazides, semicarbazides or carbazic acid esters.

For the reaction with the carboxylic acids of the formula II or reactive derivatives thereof it is advantageous to use 1–5 equivalents of the hydrazine or reactive hydrazine derivative, which can, at the same time, be used as the solvent. It is more preferable, however, to add an additional inert solvent. Suitable inert solvents are preferably alcohols, such as methanol, ethanol, isopropanol, n-butanol, isoamyl alcohol, glycols and ethers thereof, such as ethylene glycol, diethylene glycol, ethylene glycol monomethyl or monoethyl ether (methylglycol or ethylglycol), carboxylic acids, such as formic, acetic or propionic acid, and also ethers, especially water-soluble ethers, such as tetrahydrofuran, dioxane or ethylene glycol dimethyl ether (diglyme); and also water and mixtures of these solvents with one another, especially mixtures with water, for example aqueous ethanol. It is also possible to add, as a catalyst, an acid such as sulfuric acid or p-toluenesulfonic acid. The reaction temperatures are preferably between 0° and 200°, preferentially between 20° and 100°, and the reaction times are preferably between about 1 and 48 hours.

It is also possible to convert a functional group in a compound of the formula I into another functional group in a manner known per se.

Thus, in particular, it is possible to convert a halogen atom (R=F, Cl, Br or I) into a group wherein R=$R^1R^2N$ by reaction with ammonia or an amine of the formula $R^1R^2NH$ (for example methylamine, ethylamine, benzylamine, N-benzyl-N-methylamine or N-benzyl-N-ethylamine). This reaction is preferably carried out in one of the inert solvents indicated, preferentially methanol, ethanol, isopropanol or n-butanol, with or without the addition of water, at temperatures between about 0° and about 150°, preferably between 20° and 120°, and under pressures between 1 and 100 bar, preferably 1 and 5 bar. It is also possible to use an excess of the amine as the solvent.

A base of the formula I can be converted by means of an acid into the appropriate acid addition salt. Acids suitable for this reaction are, in particular, those which afford physiologically acceptable salts. Thus it is possible to use inorganic acids, for example sulfuric acid, nitric acid, hydrogenhalide acids such as hydrochloric acid or hydrobromic acid, phosphoric acids, such as orthophosphoric acid, or sulfamic acid, and also organic acids, in particular aliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids or laurylsulfuric acid. Salts with acids which are not physiologically acceptable, for example picrates, can be used to purify the compounds of the formula I.

If desired, the free bases of the formula I can be set free from their salts by treatment with strong bases, such as sodium hydroxide or carbonate or potassium hydroxide or carbonate.

Compounds of the formula I can contain one or more chiral centers. In this case they are usually present in a racemic form. Resulting racemates can be resolved into their enantiomers mechanically or chemically by methods known per se. It is preferable to form diastereomers from the racemic mixture by reaction with an optically active resolving agent. Examples of suitable resolving agents are optically active acids, such as the D-forms and L-forms of tartaric acid, diacetyltartaric acid, dibenzoyltartaric acid, mandelic acid, malic acid, lactic acid or the various optically active camphorsulfonic acids, such as β-camphorsulfonic acid. Optically active sorbent agents are also very suitable for resolution.

It is also possible, of course, to obtain optically active compounds of the formula I by the methods described above if starting materials which are already optically active are used.

The invention also relates to the use of the compounds of the formula I and their physiologically acceptable salts for the preparation of pharmaceutical formulations, in particular by a non-chemical route. In this regard they can be brought into a suitable dosage form together with at least one solid, liquid and/or semi-liquid excipient or auxiliary and, if appropriate, in combination with one or more further active compounds.

The invention also relates to pharmaceutical formulations containing at least one compound of the formula I and/or one of its physiologically acceptable salts.

These formulations can be used as medicaments in human or veterinary medicine. Suitable excipients are organic or inorganic substances which are suitable for enteral (for example oral) or parenteral administration or for topical application and which do not react with the new compounds, for example water, vegetable oils, benzyl alcohols, polyethylene glycols, glycerol triacetate, gelatine, carbohydrates, such as lactose or starch, magnesium stearate, talc or petroleum jelly. Tablets, coated tablets, capsules, syrups, elixirs or drops are especially used for oral administration, suppositories are especially used for rectal administration, solutions, preferably oily or aqueous solutions, and also suspensions, emulsions or implants are especially used for parenteral administration, while ointments, creams or powders are used for topical application. The new compounds can also be lyophilized, and the resulting lyophilisates can be used, for example, for the preparation of injection formulations. The formulations indicated can be sterilized and/or can contain auxiliaries, such as lubricants, preservatives, stabilizers and/or wetting agents, emulsifiers, salts for influencing the osmotic pressure, buffer substances, colorants, flavourings and/or aroma substances. If desired, they can also contain one or more further active compounds, for example one or more vitamins.

The invention also relates to the use of the compounds of the formula I in combating diseases, in particular cardiac insufficiency, and to their use in the therapeutic treatment of the human body or an animal body.

In this respect, the substances according to the invention are administered, as a rule, analogously to known substances having a positive inotropic action, such as Amrinon, preferably in dosages between about 1 and 100 mg, in particular between 2 and 20 mg per dosage unit. The daily dosage is preferably between about 0.02 and 2, in particular between 0.04 and 0.4 mg/kg of body weight. The particular dose for each specific patient depends, however, on a very wide variety of factors, for example on the effectiveness of the particular compound employed, on the age, body weight, general state of health and the sex, on the diet, on the time and means of administration and on the excretion rate, combination of medicaments and the severity of the particular disease to which the therapy applies. Oral administration is preferred. In comparison with the digitalis glycosides hitherto used for the therapy of cardiac insufficiency, the compounds of the formula I are distinguished by an improved therapeutic therapeutic range and peripheral relief.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire text of all applications, patents and publications, if any, cited above and below are hereby incorporated by reference.

EXAMPLES

EXAMPLE 1

920 g of 3-(4-chloro-3-nitrobenzoyl)-butyric acid are added to a mixture of 6.8 l of acetic acid and 499 g of hydrazine hydrate, and the mixture is stirred for 2 hours at 95°-100°. It is poured into ice water, and filtration gives 6-(4-chloro-3-nitrophenyl)-5-methyl-2,3,4,5-tetrahydropyridazin-3-one, m.p. 186°-188°.

The following are obtained analogously:
6-(4-chloro-3-nitrophenyl)-2,3,4,5-tetrahydropyridazin-3-one
6-(4-fluoro-3-nitrophenyl)-5-methyl-2,3,4,5-tetrahydropyridazin-3-one, m.p. 190°-193°
6-(4-bromo-3-nitrophenyl)-5-methyl-2,3,4,5-tetrahydropyridazin-3-one
6-(4-iodo-3-nitrophenyl)-5-methyl-2,3,4,5-tetrahydropyridazin-3-one
6-(4-chloro-3-nitrophenyl)-5-ethyl-2,3,4,5-tetrahydropyridazin-3-one.

EXAMPLE 2

6-(4-Chloro-3-nitrophenyl)-2,5-dimethyl-2,3,4,5-tetrahydropyridazin-3-one, m.p. 91°–92° is obtained analogously to Example 1 by means of methylhydrazine.

The following are obtained analogously
6-(4-chloro-3-nitrophenyl)-2-methyl-2,3,4,5-tetrahydropyridazin-3-one
6-(4-fluoro-3-nitrophenyl)-2,5-dimethyl-2,3,4,5-tetrahydropyridazin-3-one
6-(4-bromo-3-nitrophenyl)-2,5-dimethyl-2,3,4,5-tetrahydropyridazin-3-one
6-(4-iodo-3-nitrophenyl)-2,5-dimethyl-2,3,4,5-tetrahydropyridazin-3-one
6-(4-chloro-3-nitrophenyl)-2-ethyl-5-methyl-2,3,4,5-tetrahydropyridazin-3-one.

EXAMPLE 3

A mixture of 5 g of 6-(4-chloro-3-nitrophenyl)-5-methyl-2,3,4,5-tetrahydropyridazin-3-one, 50 ml of 25% aqueous $NH_3$ solution and 50 ml of ethanol is heated at 100° for 16 hours. The mixture is poured into ice water and extracted with methylene dichloride, the phases are separated and the organic phase is dried over sodium sulfate and evaporated to give 6-(4-amino-3-nitrophenyl)-5-methyl-2,3,4,5-tetrahydropyridazin-3-one, m.p. 234°–238°.

The following are obtained analogously by means of ammonia or the corresponding amines:
6-(4-amino-3-nitrophenyl)-2,3,4,5-tetrahydropyridazin-3-one
6-(4-methylamino-3-nitrophenyl)-5-methyl-2,3,4,5-tetrahydropyridazin-3-one
6-(4-ethylamino-3-nitrophenyl)-5-methyl-2,3,4,5-tetrahydropyridazin-3-one
6-(4-dimethylamino-3-nitrophenyl)-5-methyl-2,3,4,5-tetrahydropyridazin-3-one
6-(4-N-benzyl-N-methylamino-3-nitrophenyl)-5-methyl-2,3,4,5-tetrahydropyridazin-3-one, m.p. 136°–138°
6-(4-N-benzyl-N-ethylamino-3-nitrophenyl)-5-methyl-2,3,4,5-tetrahydropyridazin-3-one, m.p. 138°–140° ("B").

EXAMPLE 4

100 g of 6-(4-amino-3-nitrophenyl)-5-methyl-2,3,4,5-tetrahydropyridazin-3-one are dissolved in 2 l of methanol and hydrogenated over 20 g of 5% palladium-on-charcoal at 20° and 1 bar until absorption ceases. Filtration and evaporation give 6-(3,4-diaminophenyl)-5-methyl-2,3,4,5-tetrahydropyridazin-3-one, m.p. 195°–196°.

6-(3-Amino-4-methylaminophenyl)-5-methyl-2,3,4,5-tetrahydropyridazin-3-one or 6-(3-amino-4-ethylaminophenyl)-5-methyl2,3,4,5-tetrahydropyridazin-3-one are obtained analogously by hydrogenating 6-(4-N-benzyl-N-methylamino-3-nitrophenyl)-5-methyl-2,3,4,5-tetrahydropyridazin-3-one or "B", respectively.

The examples below relate to pharmaceutical formulations containing compounds of the formula I or acid addition salts thereof:

TABLETS

Example A

A mixture of 1 kg of "B" (see Example 4), 4 kg of lactose, 1.2 kg of potato starch, 0.2 kg of talc and 0.1 kg of magnesium stearate is compressed in a customary manner to give tablets in such a way that each tablet contains 10 mg of active compound.

Example B: Coated tablets

Tablets are compressed analogously to Example A and are then coated in a customary manner with a coating of sucrose, potato starch, talc, tragacanth and a colorant.

Example C: Capsules 1 kg of "B" is filled in a customary manner into hard gelatin capsules so that each capsule contains 5 mg of active compound.

Example D: Ampoules

A solution of 1 kg of "B" hydrochloride in 100 l of twice distilled water is filtered under sterile conditions, filled into ampoules, lyophilized under sterile conditions and sealed in a sterile manner. Each ampoule contains 2 mg of active compound.

Tablets, coated tablets, capsules and ampoules containing one or more of the remaining active compounds of the formula I and/or physiologically acceptable acid addition salts thereof can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pyridazinone derivative of the formula

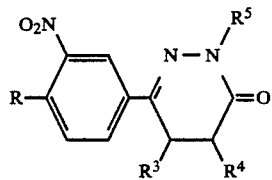

wherein
R is F, Cl, Br, I or $R^1R^2N$,
$R^1$ and $R^2$ are each independently H, $C_{1-4}$-alkyl or benzyl,
$R^3$, $R^4$ and $R^5$ are each independently H or $C_{1-4}$-alkyl, or a pharmaceutically acceptable salt thereof, wherein, if R is benzylamino, $R^3$ is $CH_3$ and $R^4$ is H, $R^5$ is $C_{1-4}$-alkyl.

2. A compound of claim 1, wherein R is $R^1R^2N$.

3. A compound of claim 2, wherein $R^1$ and $R^2$ are each independently H, $C_{1-3}$-alkyl or benzyl, and $R^3$, $R^4$ and $R^5$ are each independently H or $C_{1-3}$-alkyl.

4. A compound of claim 2, wherein $R^1R^2N$ is amino, methylamino, ethylamino, benzylamino, N-benzyl-N-methylamino or N-benzyl-N-ethylamino.

5. A compound of claim 2, $R^1R^2N$ is propylamino, dimethylamino, methylethylamino, diethylamino, dipropylamino, isopropylamino, butylamino, isobutylamino, sec-butylamino, tert-butylamino, diisopropylamino, dibutylamino, diisobutylamino, di-sec-butylamino, di-tert-butylamino, dibenzylamino, N-benzyl-N-propylamino, N-benzyl-N-butylamino, N-benzyl- N-isobutylamino, N-benzyl-N-sec-butylamino or N-benzyl-N-tert-butylamino.

6. A compound of claim 1, wherein R is F, Cl or $NH_2$.
7. A compound of claim 2, wherein $R^1$ and $R^2$ are H, methyl, ethyl or benzyl.
8. A compound of claim 1, wherein $R^3$ is methyl.
9. A compound of claim 1, wherein $R^4$ and $R^5$ are H or $CH_3$.
10. A compound of claim 7, wherein $R^3$ and $R^5$ are each independently H or $CH_3$ and $R^4$ is H.
11. A compound of claim 12, wherein $R^3$ is $CH_3$.
12. A compound of claim 7, wherein $R^3$ is $CH_3$, $R^4$ is H and $R^5$ is H or $CH_3$.
13. 6-(4-Chloro-3-nitrophenyl)-5-methyl-2,3,4,5-tetrahydropyridazin-3-one or 6-(4-amino-3-nitrophenyl)-5-methyl-2,3,4,5-tetrahydropyridazin-3-one, each a compound of claim 1.
14. 6-(4-chloro-3-nitrophenyl)-2,3,4,5-tetrahydropyridazin-3-one,
6-(4-fluoro-3-nitrophenyl)-5-methyl-2,3,4,5-tetrahydropyridazin-3-one,
6-(4-bromo-3-nitrophenyl)-5-methyl-2,3,4,5-tetrahydropyridazin-3-one,
6-(4-iodo-3-nitrophenyl)-5-methyl-2,3,4,5-tetrahydropyridazin-3-one,
6-(4-chloro-3-nitrophenyl)-5-ethyl-2,3,4,5-tetrahydropyridazin-3-one,
6-(4-chloro-3-nitrophenyl)-2,5-dimethyl-2,3,4,5-tetrahydropyridazin-3-one,
6-(4-chloro-3-nitrophenyl)-2-methyl-2,3,4,5-tetrahydropyridazin-3-one,
6-(4-fluoro-3-nitrophenyl)-2,5-dimethyl-2,3,4,5-tetrahydropyridazin-3-one,
6-(4-bromo-3-nitrophenyl)-2,5-dimethyl-2,3,4,5-tetrahydropyridazin-3-one,
6-(4-iodo-3-nitrophenyl)-2,5-dimethyl-2,3,4,5-tetrahydropyridazin-3-one,
6-(4-chloro-3-nitrophenyl)-2-ethyl-5-methyl-2,3,4,5-tetrahydropyridazin-3-one,
6-(4-amino-3-nitrophenyl)-2,3,4,5-tetrahydropyridazin-3-one,
6-(4-methylamino-3-nitrophenyl)-5-methyl-2,3,4,5-tetrahydropyridazin-3-one,
6-(4-ethylamino-3-nitrophenyl)-5-methyl-2,3,4,5-tetrahydropyridazin-3-one,
6-(4-dimethylamino-3-nitrophenyl)-5-methyl-2,3,4,5-tetrahydropyridazin-3-one,
6-(4-N-benzyl-N-methylamino-3-nitrophenyl)-5-methyl-2,3,4,5-tetrahydropyridazin-3-one,
6-(4-N-benzyl-N-ethylamino-3-nitrophenyl)-5-methyl-2,3,4,5-tetrahydropyridazin-3-one,
each a compound of claim 1.
15. A pharmaceutical composition comprising a compound of claim 1 and a pharmaceutically acceptable carrier.
16. A pharmaceutical composition comprising about 1–100 mg of a compound of claim 1 and a pharmaceutically acceptable carrier.
17. A pharmaceutical composition comprising about 2–20 mg of a compound of claim 1 and a pharmaceutically acceptable carrier.
18. A method of treating cardiac insufficiency in a patient in need of such treatment comprising administering an effective amount of a compound of claim 1.
19. A method according to claim 18, comprising administering daily dosages of about 0.02 to 2 mg/kg of body weight.
20. A method of inducing an antithrombotic effect comprising administering a compound of claim 1.

* * * * *